United States Patent

Denis et al.

[11] Patent Number: 5,977,375
[45] Date of Patent: *Nov. 2, 1999

[54] ESTERS OF BACCATIN III AND 10-DEACETYLBACCATIN III

[75] Inventors: Jean-Noel Denis; Andrew-Elliot Greene, both of Uriage; Jean-Manuel Mas, Villeurbanne, all of France

[73] Assignee: Rhone-Poulenc Rorer S.A., Antony, France

[*] Notice: This patent is subject to a terminal disclaimer.

[21] Appl. No.: 08/962,452

[22] Filed: Oct. 31, 1997

Related U.S. Application Data

[62] Division of application No. 08/411,691, filed as application No. PCT/FR93/00965, Oct. 4, 1993, Pat. No. 5,717,103.

[30] Foreign Application Priority Data

Oct. 5, 1992 [FR] France .................................. 92 11739

[51] Int. Cl.⁶ ...................... C07D 263/04; C07D 305/14
[52] U.S. Cl. ......................... 548/215; 549/510; 549/511
[58] Field of Search .................. 548/215; 549/510, 549/511

[56] References Cited

U.S. PATENT DOCUMENTS

| | | | |
|---|---|---|---|
| Re. 34,277 | 6/1993 | Denis et al. | 549/510 |
| 4,924,011 | 5/1990 | Denis et al. | 549/510 |
| 5,476,954 | 12/1995 | Bourzat et al. | 549/510 |
| 5,677,462 | 10/1997 | Mas et al. | 548/215 |
| 5,726,318 | 3/1998 | Commercon et al. | 548/215 |

*Primary Examiner*—Ba K. Trinh
*Attorney, Agent, or Firm*—Finnegan, Henderson, Farabow, Garrett & Dunner, L.L.P.

[57] ABSTRACT

A compound of the formula I:

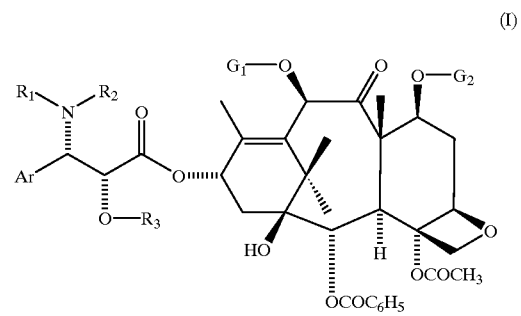

wherein

Ar represents an aryl radical;

$R_1$ represents a hydrogen atom, an aroyl radical, or a radical of the formula $R_4$—O—CO;

$R_2$ and $R_3$ together form a 5- or 6-membered saturated heterocycle;

$G_1$ represents an acetyl radical or a protecting group of the hydroxyl functional group; and $G_2$ represents a protecting group of the hydroxyl functional group.

6 Claims, No Drawings

ESTERS OF BACCATIN III AND 10-DEACETYLBACCATIN III

This is a Rule 60 Divisional of application Ser. No. 08/411,691 filed Apr. 5, 1995, now U.S. Pat. No. 5,717,103, which is a 371 of PCT/FR 93/00965 dated Oct. 4, 1993.

The present invention relates to the preparation of esters of baccatin III and of 10-deacetylbaccatin III of general formula:

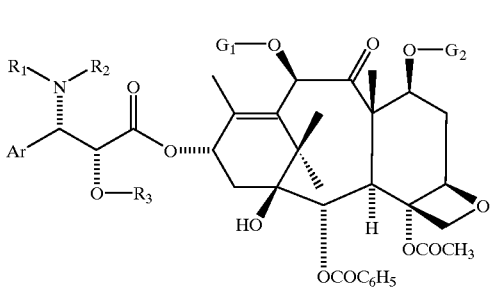

(I)

by esterification of suitably protected baccatin III or 10-deacetylbaccatin III of general formula:

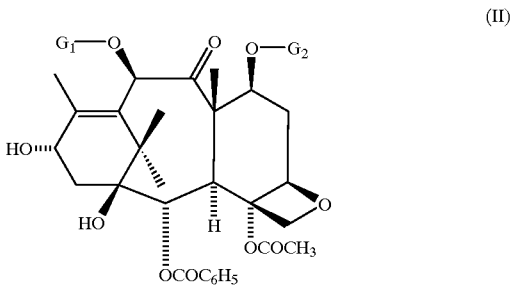

(II)

using an activated acid of general formula:

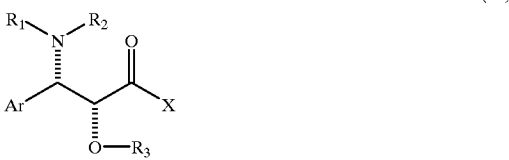

(III)

In the general formulae (I), (II) and (III), the various symbols are defined in the following way:

Ar represents an aryl radical, or else a) $R_1$ represents an aroyl radical or a radical of formula $R_4$—O—CO— in which $R_4$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms or a bicycloalkyl radical containing 7 to 10 carbon atoms, these radicals optionally being substituted by one or a number of substituents chosen from halogen atoms and hydroxyl radicals, alkyloxy radicals containing 1 to 4 carbon atoms, dialkylamino radicals in which each alkyl part contains 1 to 4 carbon atoms, piperidino radicals, morpholino radicals, 1-piperazinyl radicals (optionally substituted in 4- by an alkyl radical containing 1 to 4 carbon atoms or by a phenylalkyl radical whose alkyl part contains 1 to 4 carbon atoms), cycloalkyl radicals containing 3 to 6 carbon atoms, cycloalkenyl radicals containing 4 to 6 carbon atoms, phenyl radicals, cyano radicals, carboxyl radicals or alkyloxycarbonyl radicals in which the alkyl part contains 1 to 4 carbon atoms, or a phenyl radical optionally substituted by one or a number of atoms or radicals chosen from halogen atoms and alkyl radicals containing 1 to 4 carbon atoms or alkyloxy radicals containing 1 to 4 carbon atoms, or a saturated or unsaturated nitrogenous heterocyclic radical containing 4 to 6 members and optionally substituted by one or a number of alkyl radicals containing 1 to 4 carbon atoms, it being understood that the cycloalkyl, cycloalkenyl or bicycloalkyl radicals can optionally be substituted by one or a number of alkyl radicals containing 1 to 4 carbon atoms, $R_2$ represents a hydrogen atom, and $R_3$ represents a protective group of the hydroxyl functional group, or else b) $R_1$ being defined as above and additionally being able to represent a hydrogen atom, $R_2$ and $R_3$ together form a 5- or 6-membered saturated heterocycle, $G_1$ represents an acetyl radical or a protective group of the hydroxyl functional group, $G_2$ represents a protective group of the hydroxyl functional group, and X represents an acyloxy or aroyloxy radical or a halogen atom.

More particularly, Ar and the aryl portion of the aroyl radical represented by $R_1$, which are identical or different, represent an optionally substituted phenyl or α- or β-naphthyl radical, it being possible for the substituents to be chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, it being understood that the alkyl radicals and the alkyl portions of the other radicals contain 1 to 4 carbon atoms, the alkenyl and alkynyl radicals contain 3 to 8 carbon atoms and that the aryl radicals are phenyl or α- or β-naphthyl radicals.

More particularly still, Ar and the aryl portion of the aroyl radical represented by $R_1$, which are identical or different, represent a phenyl radical optionally substituted by a chlorine or fluorine atom or by an alkyl (methyl), alkyloxy (methoxy), dialkylamino (dimethylamino), acylamino (acetylamino) or alkyloxycarbonylamino (t-butoxycarbonylamino) radical.

More particularly, $R_3$ represents a protective group of the hydroxyl functional group chosen from methoxymethyl, 1-ethoxyethyl, benzyloxymethyl, β-trimethylsilylethoxymethyl, tetrahydropyranyl, 2,2,2-trichloroethoxymethyl, 2,2,2-trichloroethoxycarbonyl or —CH$_2$—Ph radicals, in which Ph represents a phenyl radical optionally substituted by one or a number of atoms or radicals, which are identical or different, chosen from halogen atoms and alkyl radicals containing 1 to 4 carbon atoms or alkyloxy radicals containing 1 to 4 carbon atoms.

More particularly, when $R_2$ and $R_3$ together form a 5- or 6-membered saturated heterocycle, the latter represents an oxazolidine ring substituted in the 2-position by 1 or 2 substituents, which are identical or different, chosen from hydrogen atoms and alkyl radicals containing 1 to 4 carbon atoms, alkoxy radicals containing 1 to 4 carbon atoms, aralkyl radicals whose alkyl part contains 1 to 4 carbon atoms, or aryl radicals, the aryl radicals preferably being phenyl radicals optionally substituted by one or a number of alkyloxy radicals containing 1 to 4 carbon atoms, and it being possible for the 2 substituents in the 2-position to form, with the carbon atom to which they are bonded, a ring having from 4 to 7 members, or else an oxazolidine ring substituted in the 2-position by a trihalomethyl radical or a phenyl radical substituted by a trihalomethyl radical, it being possible for the symbol $R_1$ additionally to represent a hydrogen atom.

More particularly, $G_1$ represents the acetyl radical or a protective group chosen from the 2,2,2-trichloroethoxycarbonyl or 2-(2-(trichloromethyl)propoxy) carbonyl radicals.

More particularly, $G_2$ represents a protective group of the hydroxyl functional group chosen from the 2,2,2-trichloroethoxycarbonyl or 2-(2-(trichloromethyl)propoxy) carbonyl or trialkylsilyl, dialkylarylsilyl, alkyldiarylsilyl or triarylsilyl radicals in which each alkyl part contains 1 to 4 carbon atoms and each aryl part preferably represents a phenyl radical.

More particularly, X represents an acyloxy radical containing 1 to 5 carbon atoms in a straight or branched chain or an aroyloxy radical in which the aryl part represents a phenyl radical optionally substituted by 1 to 5 substituents, which are identical or different, chosen from halogen atoms and nitro, methyl or methoxy radicals or else X represents a halogen atom chosen from chlorine or bromine.

More particularly still, X represents a t-butylcarbonyloxy or 2,4,6-trichlorobenzoyloxy radical or a chlorine atom.

It is known to prepare esters of general formula (I) by carrying out the preparation under the conditions described, for example, in European Patents EP-0,336,840, and corresponding U.S. Pat. No. 4,924,012 and EP-0,336,841, and corresponding U.S. Pat. No. 4,924,011 (now Reissue U.S. Pat. No. 34,277), or in International Application WO 92/09589, and corresponding U.S. Pat. No. 5,476,954. According to the known processes, the esterification of protected baccatin III or 10-deacetylbaccatin III using an acid of general formula:

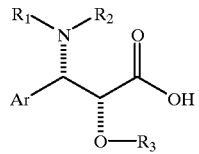

(IV)

in which Ar, $R_1$, $R_2$ and $R_3$ are defined as above, is carried out in the presence of an imide such as dicyclohexylcarbodiimide and of a dialkylaminopyridine at a temperature between 60 and 90° C.

The implementation of these processes requires the use of a significant excess of the acid of general formula (IV) with respect to the baccatin derivative.

Moreover, the use of a condensation agent such as dicyclohexylcarbodiimide can industrially pose a certain number of problems which it is important to be able to remove or reduce. In effect, dicyclohexylcarbodiimide is an expensive reagent which, due to its allergizing properties, requires specific conditions of use and which leads, during its use, to the formation of dicyclohexylurea, whose complete removal is often difficult.

It has now been found, and it is this which forms the subject of the present invention, that the esters of general formula (I) can be obtained by esterification of suitably protected baccatin III or 10-deacetylbaccatin III using an activated derivative of general formula (III) under conditions which make it possible to overcome the disadvantages mentioned above.

According to the invention, the activated derivative of general formula (III), optionally prepared in situ, is condensed with baccatin III or 10-deacetylbaccatin III in the presence of a base, preferably a nitrogenous organic base, the reaction being carried out in an inert organic solvent at a temperature between 0 and 90° C.

As nitrogenous organic bases which are particularly well suited, there may be mentioned tertiary aliphatic amines such as triethylamine, pyridine or aminopyridines such as 4-dimethylaminopyridine or 4-pyrrolidinopyridine.

As inert organic solvents, there may be mentioned ethers such as tetrahydrofuran, diisopropyl ether, methyl t-butyl ether or dioxane, ketones such as methyl isobutyl ketone, esters such as ethyl acetate, isopropyl aceopyl ether, met acetate, nitriles such as acetonitrile, aliphatic hydrocarbons such as pentane, hexane or heptane, halogenated aliphatic hydrocarbons such as dichloromethane or 1,2-dichloroethane, and aromatic hydrocarbons such as benzene, toluene or xylenes, ethylbenzene, isopropylbenzene or chlorobenzene. Aromatic hydrocarbons are of very particular advantage.

Generally, the activated derivative of general formula (III) is used in a stoichiometric amount with respect to the product of formula (II) but it can be advantageous to use up to 3 equivalents of the product of formula (III) with respect to the product of formula (II).

Generally, at least 1 equivalent of nitrogenous organic base is used with respect to the product of general formula (II) used or with respect to the derivative of general formula (III).

Preferably, esterification is carried out at a temperature in the region of 20° C.

The activated derivatives of general formula (III) can be prepared, optionally in situ, by reacting an acid halide of general formula:

$$R_5-CO-Y \qquad (V)$$

in which Y represents a halogen atom, preferably a chlorine atom, and $R_5$ represents an alkyl radical containing 1 to 5 carbon atoms in a straight or branched chain or an aryl radical preferably representing a phenyl radical optionally substituted by 1 to 5 substituents, which are identical or different, chosen from halogen atoms and nitro, methyl or methoxy radicals, or a thionyl halide, preferably the chloride, with an acid of general formula (IV).

Generally, the reaction is carried out in an inert organic solvent in the presence of a nitrogenous organic base at a temperature between 0 and 30° C.

As organic solvents, there can be used ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane, and aromatic hydrocarbons such as benzene, toluene, xylenes, ethylbenzene, isopropylbenzene or chlorobenzene.

As nitrogenous organic bases, there can be mentioned tertiary aliphatic amines such as triethylamine or pyridine or aminopyridines such as 4-dimethylaminopyridine or 4-pyrrolidinopyridine.

Generally, at least one equivalent of product of general formula (V) or thionyl halide is used with respect to the acid of general formula (IV).

The esters of general formula (I) are particularly useful for preparing taxane derivatives of general formula:

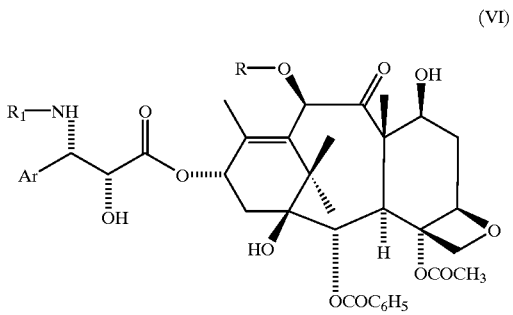

(VI)

in which Ar and $R_1$ are defined as above, which have notable antileucemic and antitumour properties.

Very particularly advantageous are the products of general formula (VI) in which, Ar being defined as above, R represents a hydrogen atom or the acetyl radical and $R_1$ represents a benzoyl or t-butoxycarbonyl radical.

The product of general formula (VI) in which R represents the acetyl radical, $R_1$ represents a benzoyl radical and Ar represents the phenyl radical is known under the name of taxol.

The product of general formula (VI) in which R represents a hydrogen atom, $R_1$ represents the t-butoxycarbonyl radical and Ar represents the phenyl radical, which is known under the name of Taxotere, forms the subject of European Patent EP 0,253,738.

The products analogous to Taxotere form the subject of International Application WO 92/09589.

According to the meanings of $R_1$, $R_2$ and $R_3$, the products of general formula (VI) can be obtained from a product of general formula (I)

either directly, when $R_1$ is defined as above, $R_2$ represents a hydrogen atom and $R_3$ represents a protective group of the hydroxyl functional group, by replacement of the protective groups $R_3$, $G_1$ and $G_2$ by hydrogen atoms or, when $R_1$ is defined as above, $R_2$ and $R_3$ together form a 5- or 6-membered heterocycle, by optionally passing through the intermediacy of a product of general formula:

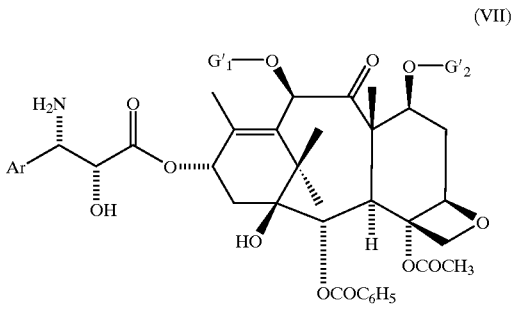

(VII)

in which $G'_1$ and $G'_2$ are identical to $G_1$ and $G_2$ and can additionally represent a hydrogen atom, which is subjected to the action of an aroyl halide or of a reactive derivative of the general formula:

$R_4$—O—CO—Z   (VIII)

in which $R_4$ is defined as above and Z represents a halogen atom or a residue —O—$R_4$ or —O—CO—O$R_4$ in which $R_4$ is defined as above, to produce a product of general formula:

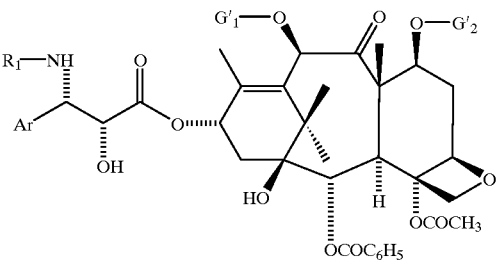

(IX)

whose protective groups $G'_1$ and $G'_2$ are replaced if necessary by hydrogen atoms.

In particular, when, in the general formula (I), $R_2$ and $R_3$ together form an oxazolidine ring which is gem-disubstituted in the 2-position, the product of general formula (VI) is obtained by passing through the intermediacy of the product of general formula (VII).

When, in the general formula (I), $R_1$ represents a radical $R_4$—O—CO— and when $R_2$ and $R_3$ together form an oxazolidine ring which is monosubstituted in the 2-position, the product of general formula (IX) in which $R_1$=$R_4$—O—CO— can be obtained directly from the product of general formula (I).

The product of general formula (VII) in which $G'_1$ represents a hydrogen atom or an acetyl radical and $G'_2$ represents a hydrogen atom can be obtained from a product of general formula (I) in which, $R_1$ representing a radical $R_4$—O—CO— in which $R_4$ represents an alkyl radical which is substituted by one or a number of halogen atoms, $R_2$ and $R_3$ together form an oxazolidine ring which is monosubstituted-or gem-disubstituted in the 2-position.

The product of general formula (VII) can also be obtained from a product of general formula (I) in which $R_1$ represents a hydrogen atom and $R_2$ and $R_3$ together form an oxazolidine ring which is substituted in the 2-position by a trihalomethyl radical or a phenyl radical substituted by a trihalomethyl radical.

The direct replacement of the protective groups $R_3$, $G_1$ and $G_2$ of a product of general formula (I) or $G'_1$ and $G'_2$ of a product of general formula (IX) by hydrogen atoms is carried out by treatment with zinc, optionally in combination with copper, in the presence of acetic acid at a temperature between 30 and 60° C. or using an inorganic or organic acid such as hydrochloric acid or acetic acid in solution in an aliphatic alcohol containing 1 to 3 carbon atoms or an aliphatic ester such as ethyl acetate, isopropyl acetate or n-butyl acetate in the presence of zinc, optionally in combination with copper, when $R_3$, $G_1$ and/or $G_2$ represent a 2,2,2-trichloroethoxycarbonyl radical, or by treatment in an acidic medium such as, for example, hydrochloric acid solution in an aliphatic alcohol containing 1 to 3 carbon atoms (methanol, ethanol, propanol, isopropanol) or aqueous hydrofluoric acid at a temperature between 0 and 40° C. when $R_3$, $G_1$ and/or $G_2$ represent a silylated radical. When $R_3$ represents a —CH$_2$—Ph group, it is necessary to replace this protective group by a hydrogen atom by hydrogenolysis in the presence of a catalyst, after having replaced the protective groups $G_1$ and $G_2$ by hydrogen atoms under the conditions described above.

The product of general formula (VII) can be obtained from a product of general formula (I) in which $R_2$ and $R_3$ together form an oxazolidine ring which is gem-disubstituted in the 2-position by treatment using formic acid, optionally in an alcohol such as ethanol or gaseous hydrochloric acid in an alcohol such as ethanol.

The product of general formula (IX) in which $R_1$ represents a radical $R_4$—O—CO— can be obtained directly from a product of general formula (I) in which $R_1$ represents a radical $R_4$—O—CO— and $R_2$ and $R_3$ together form an oxazolidine ring which is monosubstituted in the 2-position by treatment using an acid such as methanesulphonic acid at a temperature between 0 and 40° C.

The product of general formula (VII) in which $G'_1$ represents a hydrogen atom or an acetyl radical and $G'_2$ represents a hydrogen atom can be obtained from a product of general formula (I) in which $R_1$ represents a radical $R_4$—O—CO— in which $R_4$ represents an alkyl radical substituted by one or a number of halogen atoms and $R_2$ and $R_3$ form an oxazolidine ring which is monosubstituted or gem-disubstituted in the 2-position by treatment using zinc in acetic acid or electrochemically.

The product of general formula (VII) in which $G'_1$ represents an acetyl radical or a protective group of the hydroxyl functional group and $G'_2$ represents a protective group of the hydroxyl functional group can be obtained from a product of general formula (I) in which $R_1$ represents a hydrogen atom and $R_2$ and $R_3$ together form an oxazolidine ring which is substituted in the 2-position by a trihalomethyl radical or a phenyl radical substituted by a trihalomethyl radical by treatment using zinc in acetic acid.

The following examples illustrate the present invention.

EXAMPLE 1

0.321 g of (4S,5R)-5-carboxy-2,2-dimethyl-4-phenyl-3-(tert-butoxycarbonyl)-1,3-oxazolidine, 0.244 g of 2,4,6-trichlorobenzoyl chloride, 8 cm³ of anhydrous toluene and 0.101 g of triethylamine are introduced into a 50 cm³ reactor, under an inert atmosphere, at a temperature in the region of 20° C. The reaction mixture is left stirring for 2 hours at a temperature in the region of 20° C. 0.896 g of 4-acetoxy-2α-benzoyloxy-5β,20-epoxy-1β, 13α-dihydroxy-9-oxo-7β,10β-bis(2,2,2-trichloroethoxycarbonyloxy)-11-taxene and 0.122 g of 4-dimethylaminopyridine are then added. After stirring for 20 hours at a temperature in the region of 20° C., the triethylamine hydrochloride formed is separated by filtration and washed with toluene. The toluene phase is washed with 2 times 10 cm³ of water, dried over sodium sulphate and then concentrated to dryness under reduced pressure. Quantitative determination by high performance liquid chromatography shows that the 4-acetoxy-2α-benzoyloxy-5β,20-epoxy-1β-hydroxy-9-oxo-7β,10β-bis (2,2,2-trichloroethoxycarbonyloxy)-11-taxen-13α-yl (4S,5R)-2,2-dimethyl-4-phenyl-3-(tert-butoxycarbonyl)-1,3-oxazolidine-5-carboxylate yield is 77% with respect to the converted alcohol and 63% with respect to the alcohol used.

EXAMPLE 2

275 mg of (2R,3S)-3-phenyl-3-tert-butoxycarbonylamino-2-(1-ethoxyethoxy)propionic acid (0.78 mmol) in solution in 13 cm³ of anhydrous toluene are introduced, under an argon atmosphere, into a 50 cm³ round-bottomed flask equipped with a magnetic stirring system. 108.5 μl of triethylamine (0.78 mmol) and 189.5 mg of 1-chlorocarbonyl-2,4,6-trichlorobenzene (0.78 mmol) are then added successively. The reaction mixture is stirred for 54 hours at a temperature in the region of 25° C. 190.6 mg of 4-dimethylaminopyridine (1.56 mmol) are added to the colourless heterogeneous medium. The mixture is left to react for 5 minutes at a temperature in the region of 25° C. and then 116 mg (0.13 mmol) of 4-acetoxy-2α-benzoyloxy-5β,20-epoxy-1β,13α-dihydroxy-9-oxo-7β,10β-bis(2,2,2-trichloroethoxycarbonyloxy)-11-taxene are introduced. The mixture is left to react for 5 minutes at a temperature in the region of 25° C. and then the reaction mixture is heated to 72–73° C. It is left to react, with good stirring, for 64 hours at this temperature. After cooling, the orange-yellow reaction mixture is diluted with 60 cm³ of ethyl acetate. The organic phase obtained is washed 3 times with 5 cm³ of a saturated aqueous sodium bicarbonate solution, 5 times with 5 cm³ of water and 2 times with 5 cm³ of a saturated aqueous sodium chloride solution and is then dried over sodium sulphate.

After filtration and removal of the solvents under reduced pressure (2.7 kPa), a residue (488 mg) is obtained which is purified by preparative silica thin layer chromatography, eluting with an ethyl ether/dichloromethane (5/95 by volume) mixture and carrying out 2 passes.

There are thus obtained 46 mg of the starting baccatin III derivative and 69 mg of 4-acetoxy-2α-benzoyloxy-5β,20-epoxy-1β-hydroxy-9-oxo-7β,10β-bis (2,2,2-trichloroethoxycarbonyloxy)-11-taxen-13α-yl (2R,3S)-2-(1-ethoxyethoxy)-3-phenyl-3-(t-butoxycarbonylamino) propionate whose structure is confirmed by the infrared spectrum and the proton nuclear magnetic resonance spectrum.

The yield is 72% with respect to the alcohol used.

EXAMPLE 3

By carrying out the reaction in the same way as in Example 1 but replacing 2,4,6-trichlorobenzoyl chloride with 0.120 g of pivaloyl chloride, 1.16 g of crude product are obtained whose quantitative determination by high performance liquid chromatography shows that the 4-acetoxy-2α-benzoyloxy-5β,20-epoxy-1β-hydroxy-9-oxo-7β,10β-(2,2,2-trichloroethoxycarbonyloxy)-11-taxen-13α-yl (4S,5R)-2,2-dimethyl-4-phenyl-3-(tert-butoxycarbonyl)-1,3-oxazolidine-5-carboxylate yield is 98% with respect to the converted alcohol and 71% with respect to the alcohol used.

EXAMPLE 4

By carrying out the reaction in the same way as in Example 1 but replacing 2,4,6-trichlorobenzoyl chloride with 0.119 g of thionyl chloride and using 0.202 g of triethylamine, there are obtained 1.36 g of crude product whose quantitative determination by high performance liquid chromatography shows that the 4-acetoxy-2α-benzoyloxy-5β,20-epoxy-1β-hydroxy-9-oxo-7β,10β-(2,2,2-trichloroethoxycarbonyloxy)-11-taxen-13α-yl (4S,5R)-2,2-dimethyl-4-phenyl-3-(tert-butoxycarbonyl)-1,3-oxazolidine-5-carboxylate yield is 93% with respect to the converted alcohol and 31% with respect to the alcohol used.

EXAMPLE 5

0.244 g of 2,4,6-trichlorobenzoyl chloride is added, over 15 minutes and at a temperature in the region of 20° C., to a stirred solution of 0.353 g of (2R,3S)-2-(1-ethoxyethoxy)-3-phenyl-3-(tert-butoxycarbonylamino) propionic acid and 0.122 g of 4-dimethylaminopyridine in 4 cm³ of toluene. The reaction mixture is kept stirring for 16 hours at a temperature in the region of 20° C. 0.448 g of 4-acetoxy-2α-benzoyloxy-5β,20-epoxy-1β,13α-dihydroxy-9-oxo-7β, 10β-bis(2,2,2-trichloroethoxycarbonyloxy)-11-taxene and 0.122 g of 4-dimethylaminopyridine are added. The mixture is kept stirring for 20 hours. Quantitative determination by high performance liquid chromatography shows that the 4-acetoxy-2α-benzoyloxy-5β,20-epoxy-1β-hydroxy-9-oxo-7β,10β-bis(2,2,2-trichloroethoxycarbonyloxy)-11-taxene (2S,3S)- and (2R,3S)-2-(1-ethoxyethoxy)-3-phenyl-3-(tert-butoxycarbonylamino)propionate yield is 58% with respect to the alcohol used and 100% with respect to the converted alcohol.

The ratio of the two epimeres (2R,3S)/(2S,3S) is 84/16.

We claim:

1. A compound of the formula I:

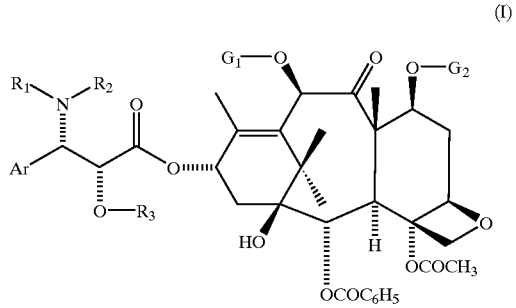

(I)

wherein

Ar represents an aryl radical;

R₁ represents a hydrogen atom, an aroyl radical, or a radical of the formula R₄—O—CO wherein R₄ represents a straight or branched alkyl radical containing 1 to 8 carbon atoms, an alkenyl radical containing 2 to 8 carbon atoms, an alkynyl radical containing 3 to 8 radical containing 7 to 10 carbons atoms, these radicals unsubstituted or substituted by at least one substituent selected from halogen atoms and hydroxyl radicals, alkyloxy radicals containing 1 to 4 carbon atoms, dialkylamino radicals wherein each alkyl portion contains 1 to 4 carbon atoms, piperidino radicals, morpholino radicals, 1-piperazinyl radicals (unsubstituted or substituted in the 4-position by an alkyl radical containing 1 to 4 carbon atoms or by a phenylalkyl radical whose alkyl portion contains 1 to 4 carbon atoms), cycloalkyl radicals containing 3 to 6 carbon atoms, cycloalkenyl radicals containing 4 to 6 carbon atoms, phenyl radicals, cyano radicals, carboxyl radicals, or alkoxycarbonyl radicals in which the alkyl part contains 1 to 4 carbon atoms, or a phenyl radical unsubstituted or substituted by at least one atom or radical selected from halogen atoms, alkyl radicals containing 1 to 4 carbon atoms, and alkyloxy radicals containing 1 to 4 carbon atoms, or a saturated or unsaturated nitrogenous heterocyclic radical containing 4 to 6 members and unsubstituted or substituted by at least one alkyl radical containing 1 to 4 carbon atoms, wherein the cycloalkyl, cycloalkenyl, or bicycloalkyl radicals can be unsubstituted or substituted by at least one alkyl radical containing 1 to 4 carbon atoms;

R₂ and R₃ together form a 5- or 6-membered saturated heterocycle;

G₁ represents an acetyl radical or a protecting group of the hydroxyl functional group; and G₂ represents a protecting group of the hydroxyl functional group.

2. The compound according to claim 1, wherein R₁, R₂, R₃, G₁ and G₂ being defined as in claim 1, Ar and the aryl portion of the aroyl radical represented by R₁, which are identical or different, represent an unsubstituted or substituted phenyl or α- or β-naphthyl radical, the substituents are selected from halogen atoms including fluorine, chlorine, bromine, iodine and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, the alkyl radicals and alkyl portions of the other radicals contain 1 to 4 carbon atoms, the alkenyl and alkynyl radicals contain 3 to 8 carbon atoms and the aryl radicals are phenyl or α- or β-naphthyl radicals.

3. The compound according to claim 1, wherein R₁, R₂, R₃, G₁ and G₂ being defined as in claim 1, Ar and the aryl portion of the aroyl radical represented by R₁, which are identical or different, represent a phenyl radical unsubstituted or substituted by a chlorine or fluorine atom or by an alkyl, alkyloxy, dialkylamino, acylamino or alkyloxycarbonylamino radical.

4. The compound according to claim 1, wherein Ar, R, G₁ and G₂ being defined as in claim 1, R₂ and R₃ together form an oxazolidine ring which is substituted in the 2-position by 1 or 2 substituents, which are identical or different, selected from hydrogen atoms and alkyl radicals containing 1 to 4 carbon atoms, alkoxy radicals containing 1 to 4 carbon atoms, aralkyl radicals whose alkyl part contains 1 to 4 carbon atoms, or aryl radicals, the aryl radicals preferably being phenyl radicals unsubstituted or substituted by one or more alkyloxy radicals containing 1 to 4 carbon atoms, and it being possible for the 2 substituents in the 2-position to form, with the carbon atom to which they are bonded, a ring having from 4 to 7 members, or else an oxazolidine ring substituted in the 2-position by a trihalomethyl radical or a phenyl radical substituted by a trihalomethyl radical, optionally the symbol R₁ additionally represents a hydrogen atom.

5. The compound according to claim 1, wherein Ar, R₁, R₂ and R₃ being defined as in claim 1, G₁ represents the acetyl radical or a 2,2,2-trichloroethoxycarbonyl or 2-(2-(trichloromethyl)propoxy)carbonyl radical and G₂ radical or trialkylsilyl, dialkylarylsilyl, alkyldiarylsilyl or triarylsilyl radical in which each alkyl part contains 1 to 4 carbon atoms and each aryl part represents a phenyl radical. radical or trialkylsilyl, dialkylarylsilyl, alkyldiarylsilyl or triarylsilyl radical in which each alkyl part contains 1 to 4 carbon atoms and each aryl part represents a phenyl radical.

6. The compound according to claim 3, wherein said alkyl is methyl, said alkyloxy is methoxy, said dialkylamino is dimethylamino, said acylamino is acetylamino and said alkyloxycarbonylamino is t-butoxycarbonylamino radical.

* * * * *

UNITED STATES PATENT AND TRADEMARK OFFICE
CERTIFICATE OF CORRECTION

PATENT NO.   : 5,977,375
DATED        : November 2, 1999
INVENTOR(S)  : Jean-Noel Denis et al.

It is certified that error appears in the above-identified patent and that said Letters Patent is hereby corrected as shown below:

Column 9,
Line 32, after "3 to 8", insert -- carbon atoms, a cyckloalkyl radical containing 3 to 6 carbon atoms, or a bicycloalkyl --.

Column 10,
Line 50, after "$G_2$", insert -- represents a 2,2,2-trichloroethoxycarbonyl or 2-(2-(trichloromethyl)propoxy)carbonyl --.
Line 53, after "radical.", delete "radical or"; and delete lines 54-56 in their entirety.

Signed and Sealed this

Fourteenth Day of August, 2001

*Attest:*

NICHOLAS P. GODICI
*Attesting Officer*   Acting Director of the United States Patent and Trademark Office